US012635914B2

(12) United States Patent
Hashimoto et al.

(10) Patent No.: US 12,635,914 B2
(45) Date of Patent: May 26, 2026

(54) PERSPIRATION AMOUNT MEASURING DEVICE AND PERSPIRATION AMOUNT MEASURING SYSTEM

(71) Applicants: Public University Corporation Suwa University of Science Foundation, Nagano (JP); Canal Water Co., Ltd., Nagano (JP)

(72) Inventors: Nobuaki Hashimoto, Nagano (JP); Tsukasa Kosuda, Nagano (JP)

(73) Assignees: Public University Corporation Suwa University of Science Foundation (JP); Canal Water Co., Ltd. (JP)

( * ) Notice: Subject to any disclaimer, the term of this patent is extended or adjusted under 35 U.S.C. 154(b) by 238 days.

(21) Appl. No.: 18/563,624

(22) PCT Filed: Feb. 1, 2023

(86) PCT No.: PCT/JP2023/003207
§ 371 (c)(1),
(2) Date: Nov. 22, 2023

(87) PCT Pub. No.: WO2023/195219
PCT Pub. Date: Oct. 12, 2023

(65) Prior Publication Data
US 2024/0268714 A1     Aug. 15, 2024

(30) Foreign Application Priority Data
Apr. 8, 2022     (JP) ................................. 2022-064656

(51) Int. Cl.
*A61B 5/145*          (2006.01)
*A61B 5/00*          (2006.01)
(52) U.S. Cl.
CPC ........ *A61B 5/14517* (2013.01); *A61B 5/6803* (2013.01); *A61B 2560/0252* (2013.01)

(58) Field of Classification Search
CPC .............. A61B 5/14517; A61B 5/6803; A61B 2560/0252; A42B 3/28; A42B 3/30
See application file for complete search history.

(56) References Cited

U.S. PATENT DOCUMENTS

2022/0142283 A1*   5/2022  Hashimoto .......... A61B 5/4266
2022/0397460 A1*  12/2022  Tokura ..................... G01K 1/14

FOREIGN PATENT DOCUMENTS

JP        2016-132835 A      7/2016
WO        2020/184686 A1     9/2020
WO      WO2020/184686    *   9/2020

OTHER PUBLICATIONS

Machine translation of WO2020/184686 (Year: 2020).*

* cited by examiner

*Primary Examiner* — Eugene T Wu
(74) *Attorney, Agent, or Firm* — Harness, Dickey & Pierce, P.L.C.

(57)          ABSTRACT

Provided is a perspiration amount measuring device that includes: an air flow path through which inside air flows; a first thermo-hygro sensor that is disposed at a place opened to an external field, and measures a temperature and a relative humidity of outside air that is taken in from a place on a side opposite to the wearer as viewed from the air flow path; a fan that sucks the inside air in the air flow path and discharges the inside air to an outside of the perspiration amount measuring device; and a second thermo-hygro sensor that is disposed in a flow of the inside air generated due to an operation of the fan, and measures a temperature and a relative humidity of the inside air. The perspiration amount measuring device is mounted on an edge portion of a helmet, and can accurately measure a head perspiration amount.

18 Claims, 10 Drawing Sheets

PERSPIRATION AMOUNT MEASURING DEVICE AND PERSPIRATION AMOUNT MEASURING SYSTEM

CROSS REFERENCE TO RELATED APPLICATIONS

This application is a 371 U.S. National Phase of International Application No. PCT/JP2023/003207, filed on Feb. 1, 2023, which claims priority to Japanese Patent Application No. 2022-064656, filed Apr. 8, 2022. The entire disclosures of the above applications are incorporated herein by reference.

TECHNICAL FIELD

The present invention relates to a perspiration amount measuring device and a perspiration amount measuring system.

BACKGROUND ART

In a site of construction work or the like, there may be a case where workers have to work in an environment of high temperature. Under such a working condition, it is necessary to prevent the workers from suffering heat stroke. If a perspiration amount of a worker working under a high temperature environment, particularly a perspiration amount of the worker from his/her whole body (a whole body perspiration amount) can be grasped real time and a measure such as rehydration or stopping of the work is taken at a state prior to suffering from heat stroke, it is effective to prevent the workers from suffering from heat stroke. However, in general, to measure a perspiration amount from the workers whole body, it is considered that a large-sized facility becomes necessary. The measurement of a perspiration amount that requires such a large-sized facility is not suitable in a site of construction work or the like (see, for example, Shinsuke Sawasaki and four others "Study on Thermal Evaluation Method for Hot Outdoor Environment" Seisan Kenkyu, 2006, volume 58, number 3, page 323 to 327, hereinafter referred to as non-patent literature 1).

To overcome such a drawback, a wearable perspiration amount measuring device has been studied by focusing on a helmet that a worker wears. Such a perspiration amount measuring device estimates a perspiration amount from the whole body by measuring a perspiration amount from a head in the helmet (see, for example, Tsukasa Kosuda and three others "Development of a Helmet Device Capable of Measuring Perspiration during Activity and Possibility of New Index for the Early Detection of Heat Stroke", Journal of Japan Institute of Electronics Packaging, General Incorporated Association "Japan Institute of Electronics Packaging", 2021, volume 24, number 6, page 541 to 550, hereinafter referred to as non-patent literature 2, and WO 2020/184686, hereinafter referred to as patent literature 1).

The perspiration amount measuring devices described in non-patent literature 2 and patent literature 1 are configured such that air existing in a space that is formed between an outer shell of a helmet and a head of a wearer (a helmet inside air flow path) can be forcibly moved by a fan. On a premise of such a configuration, a moisture amount (inflow moisture amount $X_1$) per unit volume is calculated by measuring a temperature $t_1$ and a relative humidity $RH_1$ of air that flows into the helmet inside air flow path, and a moisture amount (outflow moisture amount $X_2$) per unit volume is calculated by measuring a temperature $t_2$ and a relative humidity $RH_2$ flown out from the helmet inside air flow path. A head perspiration equivalent amount (hereinafter simply referred to as a head perspiration amount) per unit time that is generated in the helmet inside air flow path can be obtained by subtracting the inflow moisture amount $X_1$ from the calculated outflow moisture amount $X_2$ and by multiplying an amount obtained by subtraction by an air volume F.

It has been found from studies that there exists a sufficient correlation between a head perspiration amount and a whole body perspiration amount (see non-patent literature 2) and hence, the whole body perspiration amount can be estimated based on a head perspiration amount obtained in the above-mentioned manner.

In this manner, according to the perspiration amount measuring devices described in the non-patent literature 2 and the patent literature 1, a whole body perspiration amount can be measured by calculating a head perspiration amount (equivalent amount) and hence, the perspiration amount measuring devices can contribute as measures to prevent a wearer from suffering from heat stroke without using a large-sized facility.

As described above, a wearable perspiration amount measuring device that uses a helmet estimates a whole body perspiration amount based on a measured value of a head perspiration amount and hence, it is important to measure the head perspiration amount as accurately as possible.

The techniques described in non-patent literature 2 and patent literature 1 are measuring methods that are established only with respect to a particular helmet that is equipped with a fan. However, in a site of construction work or the like, helmets that are manufactured by various manufacturers are used. Accordingly, the measurement of a perspiration amount on the premise of the particular helmet equipped with a fan is difficult to spread. As described above, in a site of construction work or the like, there has been a demand for a perspiration amount measuring device that can be popularly mounted also on a helmet for general use that is not equipped with a fan and can measure a head perspiration amount more accurately.

The present invention has been made to overcome above-mentioned drawback, and it is an object of the present invention to provide a perspiration amount measuring device that can be popularly mounted on also a helmet for general use that is not equipped with a fan, and can measure a head perspiration amount more accurately compared to the prior art. It is another object of the present invention to provide a perspiration amount measuring system provided with such a perspiration amount measuring device.

SUMMARY

According to an aspect of the present invention, there is provided a perspiration amount measuring device that is mountable on an edge portion of a helmet and is capable of measuring a perspiration amount from a head of a wearer of the helmet.

The perspiration amount measuring device includes: an air flow path through which air containing vapor generated from a head (hereinafter referred to as "inside air") flows; a first thermo-hygro sensor that is disposed at a place opened to an external field, and measures a temperature and a relative humidity of air that is taken in from a place on a side opposite to the wearer as viewed from the air flow path (hereinafter referred to as "outside air"); a fan that sucks the inside air in the air flow path and discharges the inside air to an outside of the perspiration amount measuring device; and a second thermo-hygro sensor that is disposed in a flow of the inside air generated due to an operation of the fan, and measures a temperature and a relative humidity of the inside air.

According to another aspect of the present invention, there is provided a perspiration amount measuring system that includes: a helmet; and the above-described perspiration amount measuring device that is mounted on an edge portion of the helmet.

Advantageous Effects of Invention

According to the present invention, it is possible to provide the perspiration amount measuring device that can be popularly mounted on also a helmet for general use that is not equipped with a fan, and can measure a head perspiration amount more accurately compared to the prior art.

BRIEF DESCRIPTION OF THE DRAWINGS

FIG. 7 is a block diagram illustrating one example of the electrical hardware configuration mounted on the perspiration amount measuring device 1, 2 or the like.

DETAILED DESCRIPTION OF EMBODIMENTS

Hereinafter, the description is made with respect to a perspiration amount measuring device and a perspiration amount measuring system according to the present invention with reference to the drawings. Symbols that are shared in common in respective embodiments can be also used to describe the contents described with respect to the respective drawings, the contents that are described already using the symbols are applicable to the explanation of other drawings and hence, the description of other drawing is omitted.

Embodiment 1

1. Configuration of Perspiration Amount Measuring Device 1 According to Embodiment 1

Figure 1:
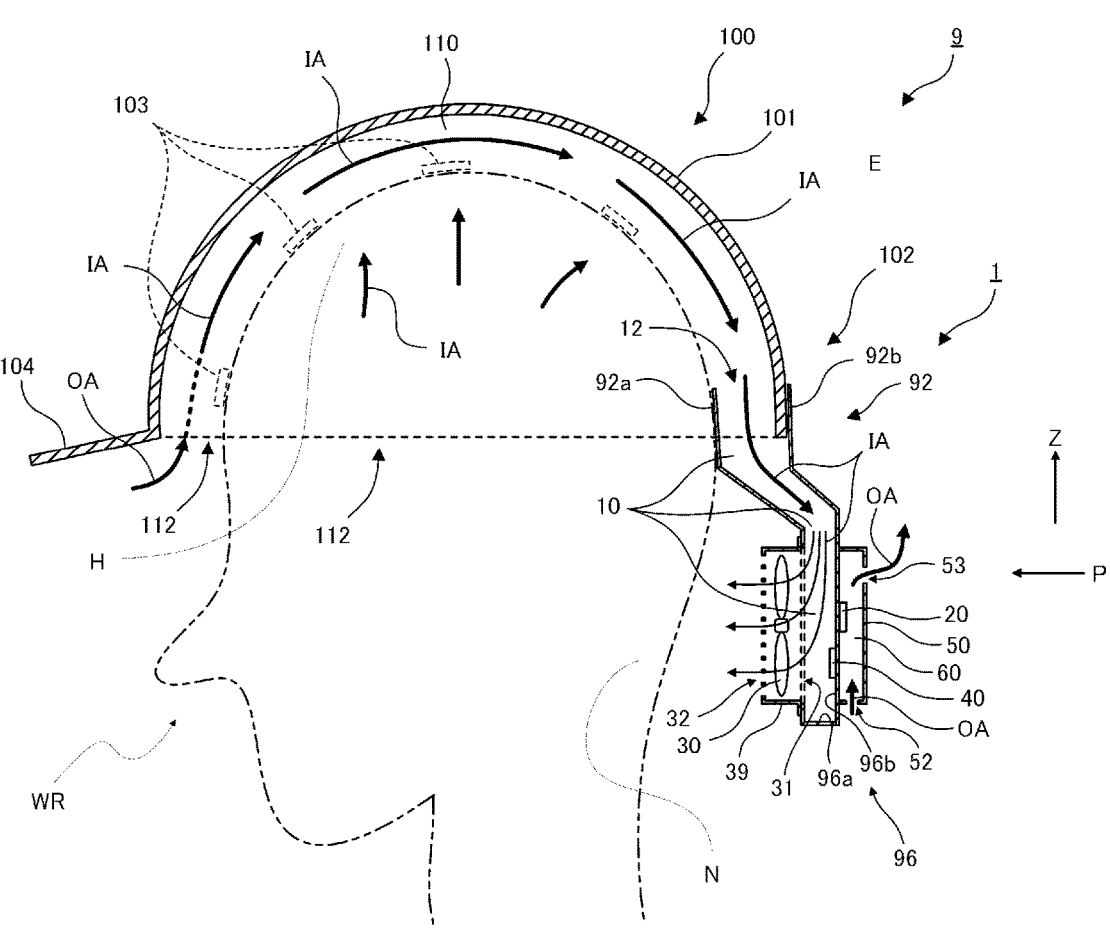
FIG. 1 is a schematic cross-sectional view of a perspiration amount measuring device 1 according to an embodiment 1 and a perspiration amount measuring system 9 according to an embodiment 3.
Figure 2:
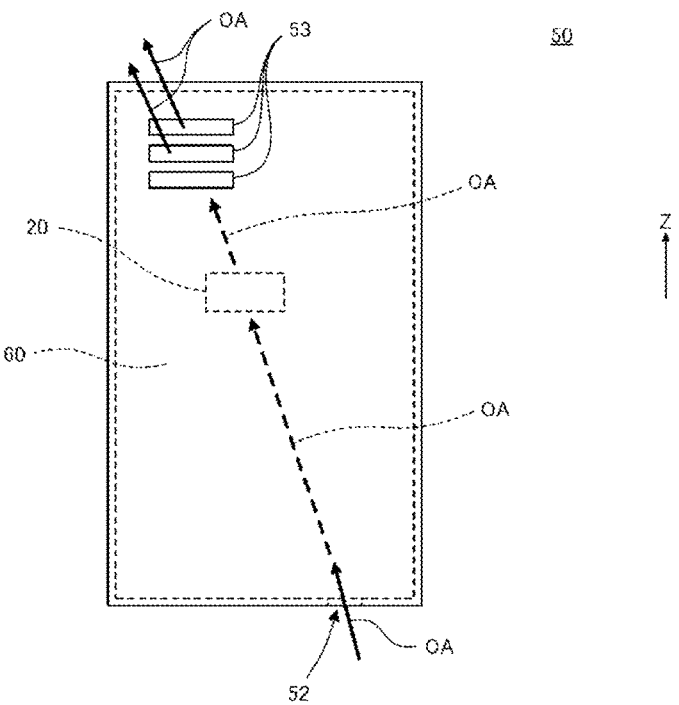
FIG. 2 is a front view illustrating only a sensor cover 50 when the perspiration amount measuring device 1 illustrated in FIG. 1 is viewed along an arrow P.

FIG. 1 is a schematic cross-sectional view illustrating a perspiration amount measuring device 1 according to the embodiment 1 and a perspiration amount measuring system 9 according to an embodiment 3. In the drawing, arrows indicated by IA, OA are provided for describing in an exemplifying manner a portion of internal air IA and a portion of an external air OA that flow in a space in a helmet. In the drawing, the directions of arrows indicate the directions that air advances (the same understanding being adopted by also in the drawings described hereinafter). FIG. 2 is a front view illustrating only a sensor cover 50 when the perspiration amount measuring device 1 illustrated in FIG. 1 is viewed along an arrow P.

(1) Summary of Perspiration Amount Measuring Device 1.

As illustrated in FIG. 1, the perspiration amount measuring device 1 according to the embodiment 1 is mounted on an edge portion 102 of a helmet 100, and is a device that measures a perspiration amount from a head H of a wearer WR of the helmet 100.

The perspiration amount measuring device 1 includes a helmet mounting means (not indicated by a symbol) that is provided for mounting the perspiration amount measuring device 1 on the helmet 100. The perspiration amount measuring device 1 includes a clip 92, and the clip 92 forms a helmet mounting means. The clip 92 includes a clip inner peripheral member 92a, a clip outer peripheral member 92b, and a clip side peripheral member 92c (see also FIG. 6A). An opening 12 is formed on one side (an upper side in the drawing) of the clip 92. When the edge portion 102 (a rear edge portion) of the helmet 100 engages with the opening 12 by fitting engagement, the edge portion 102 of the helmet 100 is fixed in a sandwiched manner between the clip inner peripheral member 92a and the clip outer peripheral member 92b. With such a configuration, the perspiration amount measuring device 1 is mounted on the helmet 100.

The perspiration amount measuring device 1 includes an air flow path 10, a first thermo-hygro sensor 20, a fan 30, and a second thermo-hygro sensor 40.

The perspiration amount measuring device 1 takes in air in an external field E (outside air OA) into the helmet 100 by rotating the fan 30, and makes air that contains vapor generated from the head H in the helmet 100 (inside air IA) flow and discharges such air from the fan 30, and measures air that flows into such a space system and air that flows out from the space system by a first thermo-hygro sensor 20 and the second thermo-hygro sensor 40.

In such a configuration, "external field E" means a region outside a region surrounded by an outer shell 101 (having a semispherical shape) of the helmet 100 and the perspiration amount measuring device 1 when the perspiration amount measuring device 1 is mounted on the helmet 100 and human wears these elements. In other words, "external field E" means a region on a side opposite to a wearer WR side with respect to the outer shell 101 of the helmet 100 or the perspiration amount measuring device 1. Further, in a narrow definition, the external field E may be also referred to as a region outside a space where the inside air IA (described later) flows.

[2] Air Flow Path 10

The air flow path 10 is a structural portion where air that contains vapor generated from the head H of the wearer WR (inside air IA) flows. The air flow path 10 is formed in a state where the air flow path 10 is surrounded by respective walls such as the clip inner peripheral member 92a and the clip outer peripheral member 92b, an inner wall 96b and a bottom 96a of a closed portion 96 described later, and a shield member 94 described later.

The air flow path 10 includes the opening 12 that is formed by one end of the clip inner peripheral member 92a and one end of the clip outer peripheral member 92b. A space that continuously extends from the opening 12 to the inside of the closed portion 96 forms the air flow path 10. The opening 12 is connected to a helmet inside air flow path 110 that is a space formed between the helmet 100 and the head H. The inside air IA can be taken into the air flow path 10 from such an opening 12.

(3) First Thermo-Hygro Sensor 20

The first thermo-hygro sensor 20 is a sensor for measuring a moisture amount X contained per unit volume in the outside air OA (also referred to as an absolute moisture X). The first thermo-hygro sensor 20 is disposed at a place opened to the external field E, and measures a temperature and a relative humidity of air in the external field E (outside air OA) that is taken in from a place on a side opposite to a side of the wearer WR as viewed from the air flow path 10. The first thermo-hygro sensor 20 is electrically connected to a control unit 70 by a wire or wireless (see FIG. 7), and transmits measured values obtained by the sensor to the control unit 70.

In the example illustrated in FIG. 1, the first thermo-hygro sensor 20 is disposed in the place on the side opposite to the side of the wearer WR as viewed from the air flow path 10 through which the inside air IA flows. More specifically, the first thermo-hygro sensor 20 is disposed on a surface of the shield member 94 on a side opposite to a surface of the shield member 94 on a wearer WR side.

(4) Sensor Cover 50

The first thermo-hygro sensor 20 can be in a state where the first thermo-hygro sensor 20 is exposed to the external field E. In a case where the perspiration amount measuring device 1 is used indoor so that the sensor cover 50 is unnecessary, the structure of the perspiration amount measuring device 1 can be simplified by eliminating the cover thus reducing the weight of the perspiration amount measuring device 1.

However, it is preferable that the first thermo-hygro sensor 20 be further covered by the sensor cover 50 so as to make the first thermo-hygro sensor 20 minimally affected by a radiation heat from the outside such as solar beams particularly. In the example illustrated in FIG. 1 and FIG. 2, the sensor cover 50 that covers the first thermo-hygro sensor 20 is mounted on the perspiration amount measuring device 1.

As illustrated in FIG. 2, an outside air intake port 52 is formed in the sensor cover 50 at a place on a side opposite to the wearer WR side as viewed from the air flow path 10 and also substantially below the first thermo-hygro sensor 20. The outside air OA is taken in from such an opening place that is not affected significantly by mixing of heat, vapor, and the like generated from the wearer WR into the outside air OA. Further, an outside air outlet port 53 is formed substantially above the first thermo-hygro sensor 20. The outside air outlet port 53 increases fluidity of air in the sensor cover 50, and suppresses irregularities in temperature generated in the sensor cover 50.

The first thermo-hygro sensor 20 spatially communicates with the external field E through the outside air intake port 52 and the outside air outlet port 53. The first thermo-hygro sensor 20 is disposed at a place opened to the external field.

The sensor cover 50 of the perspiration amount measuring device 1 includes the outside air outlet port 53 besides the outside air intake port 52. With such a configuration, the sensor cover 50 can generate the flow of the outside air OA in an inner side space where the first thermo-hygro sensor 20 is disposed. The first thermo-hygro sensor 20 is disposed in "a space 60 where the flow of the outside air OA is generated".

The perspiration amount measuring device 1 may have the configuration where the perspiration amount measuring device 1 includes only the outside air intake port 52 in the sensor cover 50 and does not include the outside air outlet port 53 in the sensor cover 50.

(5) Fan 30

The fan 30 generates a forced flow of air existing in a space system formed of the air flow path 10 and a helmet inside air flow path 110. The fan 30 is disposed adjacently to the air flow path 10.

Figure 7:
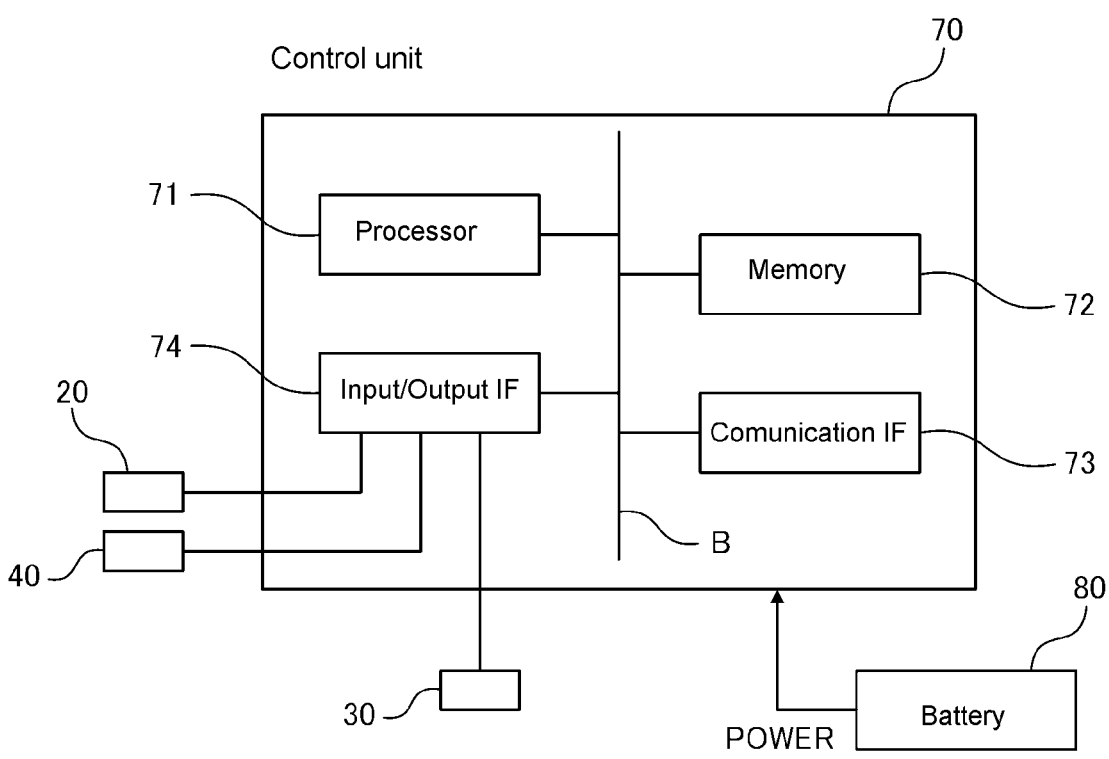

The fan 30 is electrically connected to the control unit 70 (see FIG. 7). The fan 30 is subjected to a rotation control so as to supply the air in the direction from the inside to the outside (an outside of the perspiration amount measuring device 1) of the air flow path 10 in response to a signal for driving or electricity for driving supplied from the control unit 70. With such a control, the fan 30 sucks the inside air IA in the air flow path 10, and discharges the inside air IA to the outside of the perspiration amount measuring device 1. At this point of time, a negative pressure is generated in the air flow path 10 and the helmet inside air flow path 110.

The position at which the fan 30 is disposed is set such that the discharge destination of air generated by the fan 30 is an area substantially ranging from the back of the head to the back of the neck N of the wearer WR in a state where the perspiration measuring device 1 is mounted on the edge portion 102 of the helmet 100. Assume an opening formed in the fan 30 on a side where air is taken in as a fan suction port 31, and an opening formed in the fan 30 on a side where air is discharged as a fan discharge port 32. The structure indicated by symbol 39 is a fan guard.

(6) Second Thermo-Hygro Sensor 40

The second thermo-hygro sensor 40 is a sensor for measuring a moisture amount $X_2$ (also referred to as absolute moisture $X_2$) contained per unit volume of the inside air IA.

The second thermo-hygro sensor 40 is disposed in the flow of the inside air IA generated by operating the fan 30, and measures a temperature and a relative humidity of the inside air IA. The second thermo-hygro sensor 40 is electrically connected with the control unit 70 by a wire or a wireless (see FIG. 7), and transmits a measured value obtained by the sensor to the control unit 70.

In this embodiment, with respect to the first thermo-hygro sensor 20 and the second thermo-hygro sensor 40, "thermo-hygro sensor" also takes a configuration where the temperature sensor and the moisture sensor are formed as separate bodies besides a configuration where the temperature sensor and the moisture sensor are integrally formed with each other.

(7) Closed Portion 96 of Air Flow Path 10

The air flow path 10 includes the closed portion 96 formed adjacently to the fan 30. The entire shape of the air flow path 10 is formed in a so-called dead end shape where, assuming the opening 12 as "inlet", a portion near a proximal end of the closed portion 96 (the bottom 96a of the closed portion 96) forms "a dead end".

In such a configuration, the fan 30 is disposed near the proximal end of the closed portion 96 of the air flow path 10 parallel to and adjacently to the longitudinal direction of the air flow path 10.

When the fan 30 is operated, the inside air IA that flows through the air flow path 10 is discharged from an area near the proximal end of the closed portion 96 by the fan 30. When the fan 30 is operated, a negative pressure attributed to the fan 30 is generated in the air flow path 10, and a most portion of the inside air IA concentrates near the proximal end of a space in the closed portion 96 (an area near the bottom of the space of the dead end) and the area near the fan, and passes.

It is preferable that the second thermo-hygro sensor 40 be disposed in the closed portion 96 of the air flow path 10. More specifically, it is preferable that the second thermo-hygro sensor 40 be disposed on an upstream side of the fan 30 (on a side of the fan suction port 31 as viewed from the fan 30). In the example illustrated in FIG. 1, the second thermo-hygro sensor 40 is arranged at the position on the inner wall 96b of the closed portion (in this embodiment, a wall of the shield member 94 also forming the inner wall of the closed portion) and the second thermo-hygro sensor 40 faces the fan 30.

As an opposite case, the second thermo-hygro sensor 40 may be disposed on a downstream side of the fan 30 (a side of the fan discharge port 32 as viewed from the fan 30).

(8) Measurement of Head Perspiration Amount Y

The perspiration amount measuring device 1 measures basically a head perspiration amount Y using a principle of perspiration amount measurement described in non-patent literature 2. However, in the embodiment 1, the measurement of the head perspiration amount Y is not limited to such a principle.

Assuming a space formed between the outer shell 101 of the helmet 100 and the head H of the wearer WR as a helmet inside air flow path 110, the perspiration amount measuring device 1 measures a temperature $t_1$ and a relative humidity $RH_1$ of air in the external field E that flows into the helmet inside air flow path 110 or the outside air OA that is air equivalent to the air in the external field E using the first thermo-hygro sensor 20, and calculates a moisture amount per unit volume as an inflow moisture amount $X_1$. The perspiration amount measuring device 1 also measures a temperature $t_2$ and a relative humidity $RH_2$ of the inside air IA generated in the helmet inside air flow path 110 using the second thermo-hygro sensor 40, and calculates a moisture amount per unit volume as an outflow moisture amount $X_2$. Then perspiration amount measuring device 1 calculates the head perspiration amount Y that is a perspiration amount from the head H based on the inflow moisture amount $X_1$, the outflow moisture amount $X_2$, and an air volume F relating to discharging of the inside air IA by the fan 30. More specifically, the head perspiration amount Y is calculated by subtracting the inflow moisture amount $X_1$ from the outflow moisture amount $X_2$ and by multiplying a moisture amount obtained by the subtraction by the air volume F.

Further, a whole body perspiration amount can be estimated based on the calculated head perspiration amount Y.

With the use of the measuring device that performs the measurement in accordance with such a principle, the manner of operation and advantageous effects of the perspiration amount measuring device 1 according to the embodiment 1 can be maximized. In other words, with use of the measuring device provided with the configuration of the perspiration amount measuring device 1 according to the embodiment 1, the measurement of the head perspiration amount and the whole body perspiration amount based on the above-mentioned principle can be performed more accurately.

The detail relating to the calculation of the head perspiration amount Y is described in "example" described later.

2. Simulation Example

The inventors of the present invention have obtained novel finding with respect to the arrangement position of the first thermo-hygro sensor 20 suitable for accurately measuring a head perspiration amount. This novel finding is described hereinafter.

(1) Simulation Condition

It is assumed that a man wears a helmet provided with a helmet body and a fan that is mounted on the helmet body and discharges air in the helmet. It is also assumed that vapor and heat equivalent to vapor and heat that are generated when an average person wears the helmet are generated from the inside of the helmet. It is further assumed that a fixed amount of perspiration per unit time is generated from a wearer (a person who wears the helmet). It is still further assumed that air having a speed of 1.5 [m/s] impinges on the helmet from the back of the helmet.

It is assumed that inside air in the helmet inside air flow path or the air flow path is discharged by the fan. In such an operation, it is assumed that a temperature and a relative humidity of inside air are grasped by the second thermo-hygro sensor so that an outflow moisture amount is grasped. Further, it is assumed that a temperature and a relative humidity of air in the external field (outside air) that flows into the inside of the helmet are grasped by the first thermo-hygro sensor, so that an outflow moisture amount is grasped.

As a principle used for calculating a head perspiration amount (equivalent amount) Y, a principle of a perspiration amount measuring principle described in non-patent literature 2 is used.

It is assumed that the second thermo-hygro sensor is disposed just near the fan discharge port.

The first thermo-hygro sensor is, at the first level (level 1), disposed in a place on a side opposite to a side of the wearer as viewed from the helmet inside air flow path or the air flow path. More specifically, it is assumed that the first thermo-hygro sensor is disposed outside the outer shell of the helmet. Further, the first thermo-hygro sensor is, at the second level (level 2), disposed near the inflow port of outside air in the inside of the helmet (see FIG. 1 in non-patent literature 2).

(2) Result of Simulation and Observation

Figure 3:
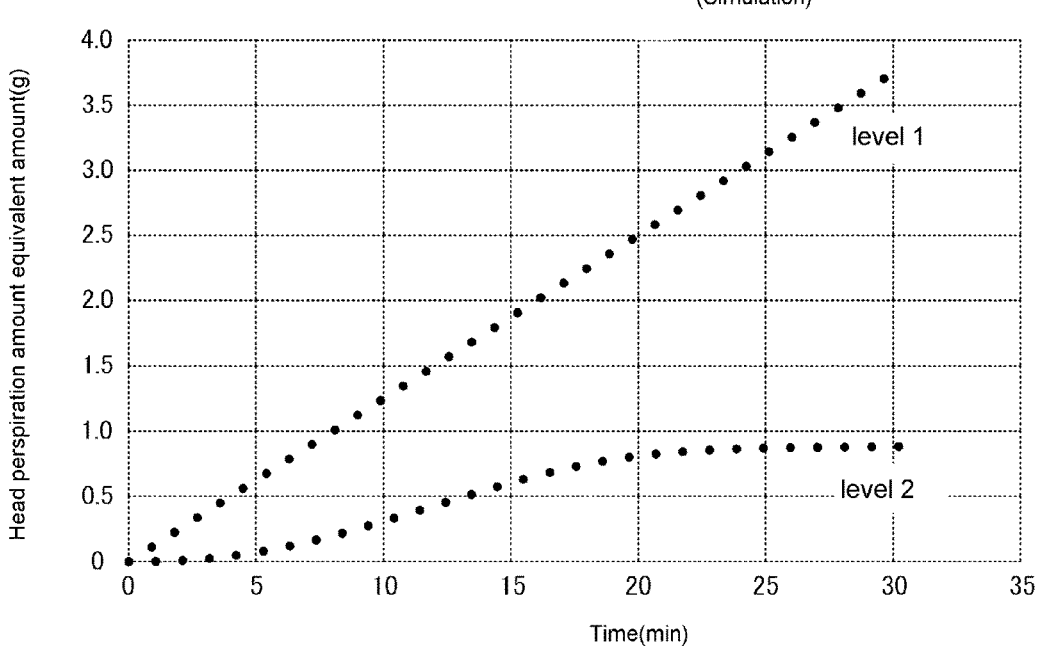
FIG. 3 is a graph plotted by calculating an accumulated amount of a head perspiration amount equivalent amount by simulation while changing levels by changing a place where a first thermo-hygro sensor 20 is disposed.

FIG. 3 is a graph plotted by calculating an accumulated amount of a head perspiration amount equivalent amount by simulation while changing the level by making the place where the first thermo-hygro sensor 20 is disposed different.

As indicated by the graph illustrated in FIG. 3, at the level 1, the head perspiration amount equivalent amount (accumulated amount) was increased linearly with the lapse of time. On the other hand, at the level 2, although the tendency that the head perspiration amount equivalent amount (accumulated value) is increased along with the lapse of time, the accumulated value was saturated when a certain time period has elapsed.

In a case where a fixed amount of perspiration per unit time is produced from a wearer, it is considered that an actual head perspiration amount (accumulated value) was also linearly increased with the lapse of time naturally. To observe the present simulation from this point, the graph was not linearly increased at the level 2. This is because that, although the arrangement position of the first thermo-hygro sensor at the level 2 was the position at which air in the external field was taken in, the position was the position where a possibility exists that heat and moisture generated from a neck, a forehead and the like of the wearer were also mixed so that the accuracy of the measurement of the head perspiration amount equivalent amount was decreased.

On the other hand, with respect to the graph at the level 1, the head perspiration amount equivalent amount (accumulated value) was increased linearly with the lapse of time, and it was found that the value close to the actual head perspiration amount was obtained when the arrangement position of the first thermo-hygro sensor at the level 1 was adopted. From the above-mentioned result of simulation, in constituting the perspiration amount measuring device 1, it was confirmed that it is preferable to arrange the first thermo-hygro sensor at the place on a side opposite to a side of a wearer as viewed from the helmet inside air flow path or the air flow path in accordance with the level 1.

3. Advantageous Effects of Perspiration Amount Measuring Device 1 According to the Embodiment 1

(1) In the perspiration amount measuring device described in non-patent literature 2, the thermo-hygro sensor (corresponding to the first thermo-hygro sensor 20) on an inflow air side is disposed near an inner periphery of the helmet. Although such a sensor arrangement position is the position at which air in the external field is taken in, there is a possibility that heat and moisture generated from a neck, a forehead, a breast, a back and the like of a wearer are mixed into air from the external field at such a position. In view of the above, with respect to the configuration of the perspiration amount measuring device described in non-patent literature 2, there is a possibility that the measurement of the heat perspiration amount is affected by the heat and the moisture from the wearer and hence, there is still room for improvement in the more accurate measurement of the head perspiration amount.

On the other hand, according to the perspiration amount measuring device 1 of the embodiment 1, the first thermo-hygro sensor 20 is disposed at the place released (opened) to the external field E and hence, the first thermo-hygro sensor 20 measures a temperature and a relative humidity of air in the external field E sucked from the place on a side opposite to a side of the wearer WR as viewed from the air flow path 10. Accordingly, near the first thermo-hygro sensor 20, fresh outside air is taken in in a state where the mixing of the head and the moisture from heat and moisture generated from a head, a neck, a forehead, a breast, a back and the like of the wearer WR is suppressed. The first thermo-hygro sensor 20 senses such air and hence, the effect of the heat and the moisture generated from the wearer WR can be suppressed whereby the head perspiration amount Y can be measured more accurately.

Further, according to the perspiration amount measuring device 1, the configuration is adopted where, using the fan 30, the inside air IA in the air flow path 10 is sucked and is discharged to the outside of the perspiration amount measuring device 1. Accordingly, the most of the inside air IA is converged to an area near the fan 30 and flows out. The second thermo-hygro sensor 40 is disposed in the flow of the inside air IA generated by the operation of the fan 30. In other words, the second thermo-hygro sensor 40 is disposed at the position where the most of the inside air IA passes and hence, the temperature $t_2$ of the inside air IA and the relative humidity $RH_2$ of the inside air IA can be appropriately sensed whereby the head perspiration amount Y can be measured more accurately.

As has been described above, the perspiration amount measuring device 1 according to the embodiment 1 can be popularly mounted also on a general-type helmet that is not equipped with a fan, and can measure a head perspiration amount more accurately compared to conventional perspiration amount measuring devices. Further, such accurate measurement can be realized with the simple configuration without increasing the number of parts, for example, the number of fans or the number of sensors.

(2) In the perspiration amount measuring device described in the non-patent literature 2, the fan is formed in a state where the fan is embedded in a portion of the outer shell of the dedicated helmet (helmet equipped with the fan) and hence, there exists a circumstance that a so-called large fan cannot be introduced. Accordingly, in the prior art, in a case where the wearer WR generates a large amount of perspiration during a short time, discharging of air by the fan cannot catch up with the generation of perspiration and hence, there arises a drawback that the measurement of a perspiration amount cannot follow a change in a perspiration generation state whereby there is still room for improvement in terms of the more accurate and precise measurement of a perspiration amount.

On the other hand, in the perspiration amount measuring device 1 according to the embodiment 1, the perspiration amount measuring device 1 measures a perspiration amount in a state where the perspiration amount measuring device 1 is mounted on a commercially available helmet externally. Naturally, the fan 30 is also mounted on the helmet body externally and hence, the degree of freedom in selecting the fan is increased. The perspiration amount measuring device 1 according to the embodiment 1 can adopt a fan that is large-sized and has a large air volume and a high efficiency compared to a fan that is incorporated in the helmet. By suitably adopting such a fan having high performance, even if the wearer WR generates a large amount of perspiration during a short time, the fan can discharge the inside air IA with sufficient ability and hence, for example, it is possible to perform the measurement that speedily follows the sharp increase of a perspiration amount. Also from this point of view, the perspiration amount measuring device can expect the measurement with high accuracy and high precision.

(3) The perspiration amount measuring device 1 according to the embodiment 1 includes the sensor cover 50 that covers the first thermo-hygro sensor 20. Since the perspiration amount measuring device 1 includes such a cover, in the same manner as a ventilated case for meteorological instruments used for weather observation, it is possible to prevent a radiation heat from sun, a ground, buildings and the like, a radiation heat, a convection heat and the like from a wearer, a moisture (vapor) that the wearer generates and the like from being directly transferred to the first thermo-hygro sensor 20. Accordingly, the first thermo-hygro sensor 20 can perform a sensing operation while suppressing direct effects from these heats, moisture and the like and hence, the head perspiration amount Y can be more accurately measured.

(4) In the first thermo-hygro sensor 20 according to the embodiment 1, the sensor cover 50 has the outside air intake port 52 and the outside air outlet port 53. With such a configuration, fluidity of air in the sensor cover 50 is increased and hence, irregularities in temperature generated in the sensor cover 50 can be suppressed.

Further, the first thermo-hygro sensor 20 is disposed in the space where the flow of the outside air OA is generated. By arranging the first thermo-hygro sensor 20 in the space where the flow of the outside air OA exists besides simply bringing the first thermo-hygro sensor 20 into contact with outside air OA, the fresh outside air OA that is not affected by heat generated by the perspiration from a human body constantly impinges on the first thermo-hygro sensor 20. Accordingly, the head perspiration amount Y can be measured more accurately.

(5) The air flow path 10 according to the embodiment 1 has the closed portion 96 formed adjacently to the fan 30, and the second thermo-hygro sensor 40 is disposed near the fan 30. In other words, the closed portion 96 is formed in the air flow path 10 (the end of the air flow path 10 being formed in a dead-end shape) and hence, the inside air IA that flows in the air flow path 10 is discharged from an area near the proximal end of the closed portion 96 by the fan 30.

With such a configuration, a negative pressure attributed to the fan 30 is generated in the air flow path 10. Accordingly, the most portion of the inside air IA can be collected to an area near the proximal end (near a bottom of a corner portion of the dead end) in the closed portion 96 and an area in the vicinity of the fan 30, and it is possible to make the most portion of the inside air IA pass through such areas. Further, in the closed portion 96, the fresh outside air OA is hardly mixed into the inside air IA. In this manner, the inside air IA with high purity that is collected at the area near the proximal end of the closed portion 96 and at the area near the fan 30 can be sensed by the second thermo-hygro sensor 40 in a stable manner and hence, the perspiration amount measurement can be performed with more accurate and higher precision.

(6) The position at which the fan 30 according to the embodiment 1 is disposed is set such that, in a state where the perspiration amount measuring device 1 is mounted on the edge portion 102 of the helmet 100, the discharge destination of air by the fan 30 becomes a region ranging from a back of the head of the wearer WR to the back of the neck N of the wearer WR. The air discharged from the fan 30 directly impinges on the region ranging from the back of the head to the area near the back of the neck of the wearer and hence, the air cools down the wearer WR or lowers a body temperature of a wearer WR thus positively contributing to the prevention of a heat stroke.

Embodiment 2

Figure 4:
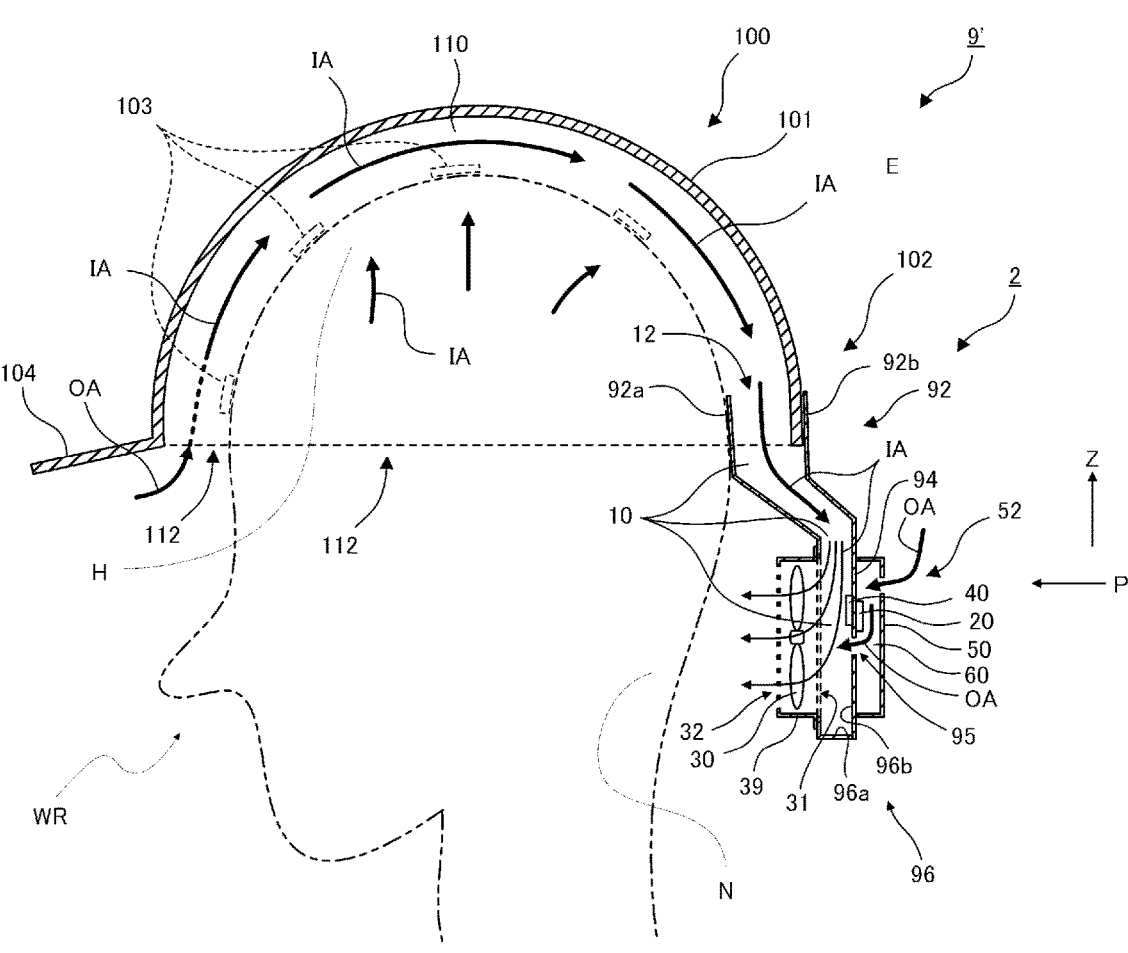
FIG. 4 is a schematic cross-sectional view illustrating a perspiration amount measuring device 2 according to an embodiment 2 and a perspiration amount measuring system 9' according to an embodiment 3.
Figure 5:
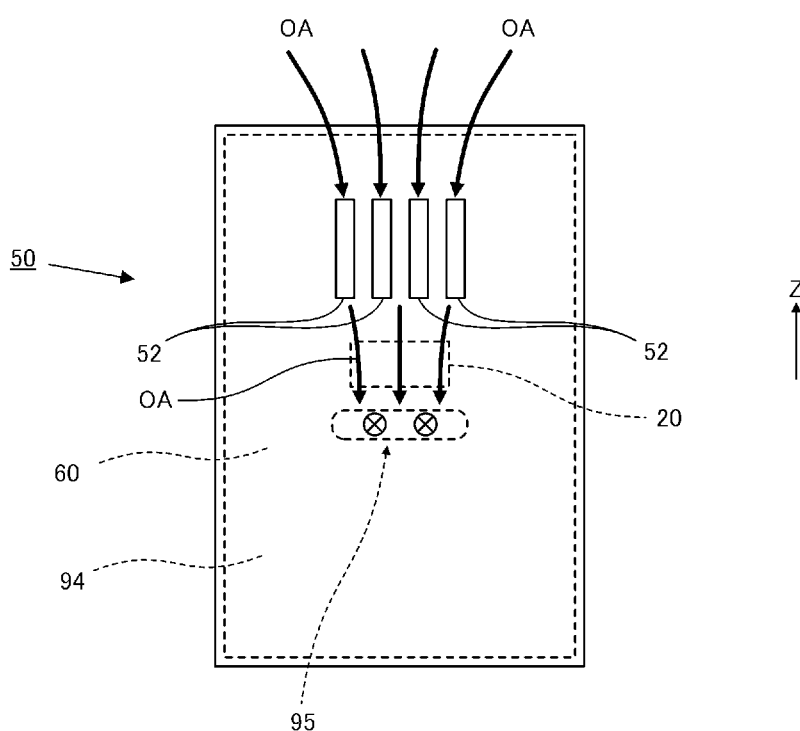
FIG. 5 is a front view illustrating only the sensor cover 50 when a perspiration amount measuring device 4 illustrated in FIG. 4 is viewed along an arrow P.

FIG. 4 is a schematic cross-sectional view illustrating a perspiration amount measuring device 2 according to an embodiment 2 and a perspiration amount measuring system 9' according to an embodiment 3. FIG. 5 is a front view illustrating only a sensor cover 50 when the perspiration amount measuring device 4 illustrated in FIG. 4 is viewed along an arrow P.

The perspiration amount measuring device 2 according to the embodiment 2 basically has substantially the same configuration as the perspiration amount measuring device 1 according to the embodiment 1. However, the perspiration amount measuring device 2 according to the embodiment 2 differs from the perspiration amount measuring device 1 according to the embodiment 1 with respect to the manner of forming the flow of the outside air OA that impinges on a first thermo-hygro sensor 20.

1. Configuration and Advantageous Effects of Perspiration Amount Measuring Device 2 According to the Embodiment 2

As illustrated in FIG. 4 and FIG. 5, the perspiration amount measuring device 2 according to the embodiment 2 is provided with a shield member 94 that includes a communicating portion 95 that is disposed between an air flow path 10 and the first thermo-hygro sensor 20. The shield member 94 forms the air flow path 10 and a space 60 where the flow of the outside air OA is generated by partitioning and hence, the shield member 94 can be also referred to as "a partition member 94".

The perspiration amount measuring device 2 has such a configuration. Accordingly, the air flow path 10 and the space where the first thermo-hygro sensor 20 is disposed communicate with each other through the communicating portion 95. As a result, when the inside air IA in the air flow path 10 is sucked by the fan 30, along with such an air sucking operation, the outside air OA is also forcibly sucked from the space where the first thermo-hygro sensor 20 is disposed through the communicating portion 95. As a result, in the space where the first thermo-hygro sensor 20 is disposed, the flow of the outside air OA (the flow of the outside air OA that flows into the space from an outside air intake port 52, passes an area near the first thermo-hygro sensor 20, and reaches the communicating portion 95) is generated.

According to the perspiration amount measuring device 2 of the embodiment 2, the flow of the outside air OA can be realized without providing a new fan and hence, it is possible to provide the perspiration amount measuring device that performs the measurement of a perspiration amount more accurately with high precision while ensuring space saving, downsizing and the reduction of weight.

The sucked outside air OA merges with the inside air IA near the communicating portion 95 in the air flow path 10. In this case, by setting an amount of the inside air IA that merges with the inside air IA to a value that is extremely small compared to an amount of the inside air IA near the fan 30 (an effect brought about by merging of the outside air OA into the inside air IA being small), it is possible to perform the practical perspiration amount measurement.

Further, the communicating portion 95 is formed at the position near the fan 30 where the communicating portion 95 faces the fan 30. By forming the communicating portion 95 at such a position, the outside air OA can be sucked more effectively.

In the perspiration amount measuring device 2, the space where the first thermo-hygro sensor 20 is disposed (the space 60 where the flow of the outside air OA is generated) is formed such that the outside air OA flows at a substantially constant amount near the first thermo-hygro sensor 20. That is, by performing the discharging of air by the fan 30 at a substantially constant amount, even in the space where the first thermo-hygro sensor is disposed (the space 60 where the flow of the outside air OA is generated), it is possible to make the outside air OA flow at a substantially constant amount.

In this manner, by adopting the configuration where the first thermo-hygro sensor 20 can perform sensing of the outside air OA having a substantially constant amount, even if a sudden and strong hot air or cool air is generated in an external field E, in the space where the first thermo-hygro sensor 20 is disposed, it is possible to perform sensing of the outside air OA in a state where an effect of disturbance caused by a sudden and strong hot air or cool air in the external field E is attenuated. Accordingly, it is possible to minimize an effect such as a sudden change in weather or the like in the external field E and hence, it is possible to perform the measurement of a head perspiration amount Y more accurately with high precision.

Further, in the perspiration amount measuring device 2, to focus on the flow of the outside air OA, the first thermo-hygro sensor 20 is disposed upstream of the communicating portion 95 and near the communicating portion 95. By arranging the first thermo-hygro sensor 20 at such a position, it is possible to measure a temperature and a relative humidity near the communicating portion into which the outside air OA is sucked and gathered and hence, a measured value of the head perspiration amount Y becomes more accurate.

In a strict sense, in the perspiration amount measuring device 2, the outside air OA that is measured by the first thermo-hygro sensor 20 is mixed into the inside air IA in a space where the second thermo-hygro sensor 40 is disposed. However, by making a mixing amount of the outside air OA into the inside air IA extremely small, an amount of air that becomes an object to be measured by the second thermo-hygro sensor 40 can be set substantially equal to an amount of the inside air IA. As a result, the measurement principle that has been described above can be established substantially in the same manner.

The perspiration amount measuring device 2 according to the embodiment 2 basically has substantially the same configuration as the perspiration amount measuring device 1 according to the embodiment 1 with respect to the configurations other than the configuration (the manner) of generating the outside air OA that impinges on the first thermo-hygro sensor 20. Accordingly, the perspiration amount measuring device 2 acquires advantageous effects corresponding to the advantageous effects amongst all advantageous effects acquired by the perspiration amount measuring device 1.

2. Example of Perspiration Amount Measuring Device 2

The perspiration amount measuring device 2 according to the example basically has substantially the same configuration as the perspiration amount measuring device 2 according to the embodiment 2 described with reference to FIG. 4. Accordingly, with respect to the constitutional elements that are substantially identical to the corresponding constitutional elements of the perspiration amount measuring device 2 according to the embodiment 2, as the description of constitutional elements, the description of the corresponding constitutional elements of the perspiration amount measuring device 2 according to the embodiment 2 is used so that the repeated explanation of these constitutional elements is omitted.

Figure 6A:
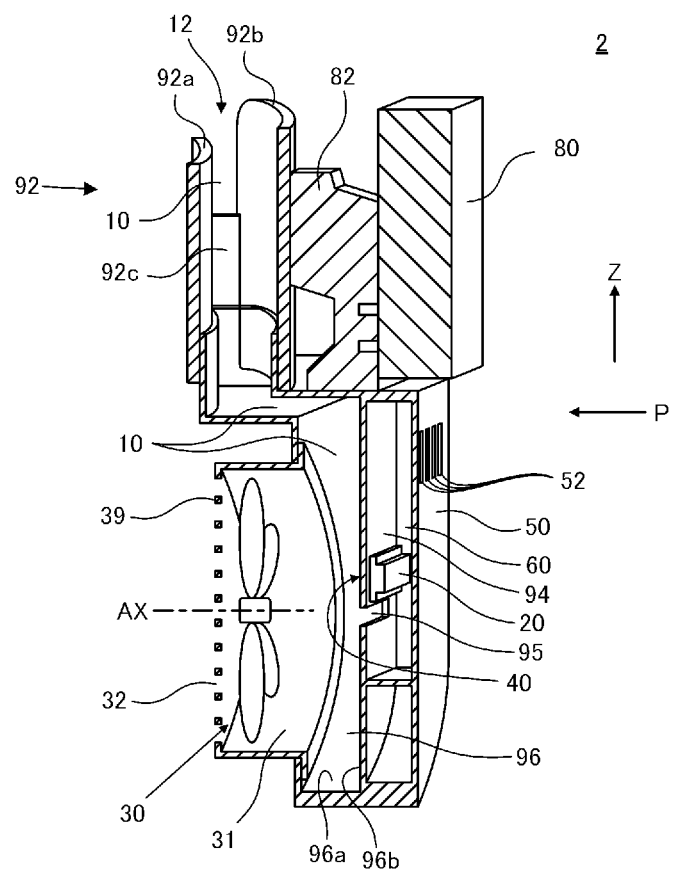
FIGS. 6A and 6B are views illustrating an embodiment of the perspiration amount measuring device 2.
Figure 6B:
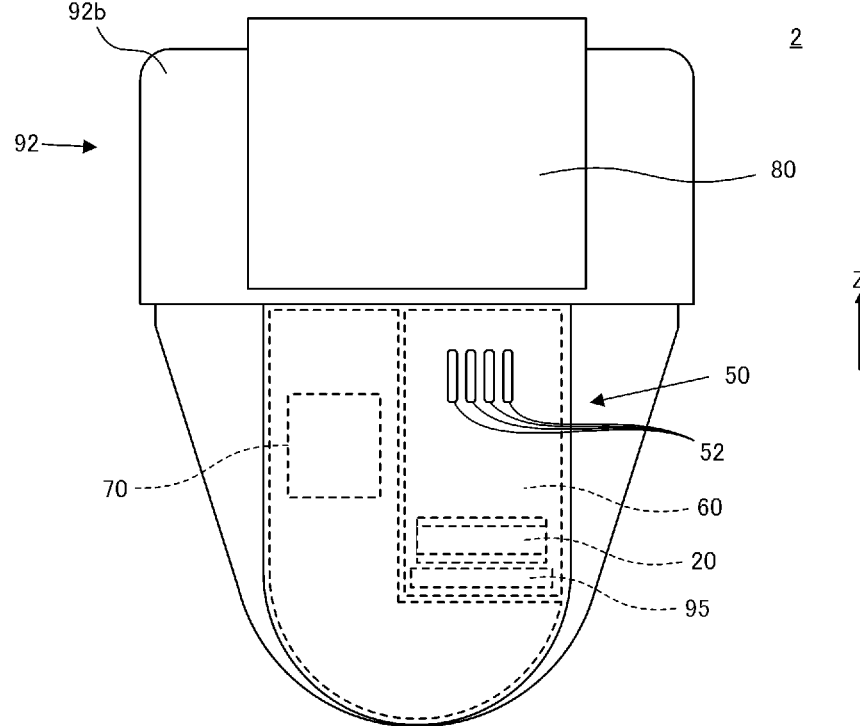

FIGS. 6A and 6B are views illustrating the example of the perspiration amount measuring device 2. FIG. 6A is a perspective cross-sectional view of the perspiration amount measuring device 2 taken along a plane that includes a rotary axis AX of a fan 30 and a longitudinal direction of the perspiration amount measuring device 2. FIG. 6B is a front view of the perspiration amount measuring device 2 when the perspiration amount measuring device 2 illustrated in FIG. 6A is viewed along an arrow P.

As illustrated in FIG. 6A, when the perspiration amount measuring device 2 is viewed from a side where an opening 12 is disposed, a clip inner peripheral member 92$a$ and a clip outer peripheral member 92$b$ are curved tracing a curvature shape of an edge portion 102 of a helmet (the illustration of the edge portion 102 being omitted in FIGS. 6A and 6B). Symbol 80 indicates a battery. The battery 80 is supported on and fixed to the clip outer peripheral member 92$b$ and a housing (not indicated by a symbol) by a battery support member 82. As illustrated in FIG. 6B, a hardware that constitutes a control unit 70 is housed in the housing (not indicated by a symbol).

FIG. 7 is a block diagram illustrating one example of the electrical hardware configuration that is mounted on the perspiration amount measuring device 1, 2 or the like. As illustrated in FIG. 7, electrically, the control unit 70 forms a central element among electrical constitutional elements of the perspiration amount measuring device according to the example. The same goes for the perspiration amount measuring device 1 according to the embodiment 1, the perspiration amount measuring device 2 according to the embodiment 2, and perspiration amount measuring devices 3, 4, 5 according to respective modifications described later.

The control unit 70 is a computer, and includes a processor 71, a memory 72 (a storage not illustrated in the drawing being also included in the concept of the memory), a communication I/F (interface) 73, and an input/output I/F (interface) 74. These are connected to a bus B.

The battery 80 supplies electricity to the control unit 70.

The processor 71 is operated in accordance with a program stored in the memory 72, and performs a control of the respective units. The memory 72 also includes a non-volatile memory device (ROM or the like). The memory 72 stores: a boot program executed by the processor 71 at the time of starting the perspiration amount measuring device 2; and a program dependent on a hardware of the control unit 70 and the like.

The communication I/F 73 performs the transmission and the reception of data with an external management device (not illustrated in the drawing) via a wireless communication unit (not indicated by a symbol).

The input/output I/F 74 is electrically connected to a first thermo-hygro sensor 20, a second thermo-hygro sensor 40, a fan 30 and the like respectively, and is operated as an interface with these input/output devices.

The processor 71 performs a rotation control of the fan 30. The processor 71 calculates a head perspiration amount Y based on information from the first thermo-hygro sensor 20 and the second thermo-hygro sensor 40 via the input/output I/F 74. Further, the processor 71 may calculate a whole body perspiration amount based on the calculated head perspiration amount Y. The processor 71 controls the data transmission/reception between the processor 71 and the management device (not illustrated in the drawing) via the communication I/F 73. The processor 71 can be operated so as to hold data relating to the calculated head perspiration amount Y or the calculated whole body perspiration amount in the memory 72.

The control unit 70 calculates a moisture amount per unit volume as an inflow moisture amount $X_1$ based on a temperature $t_1$ and a relative humidity $RH_1$ of outside air OA received from the first thermo-hygro sensor 20.

Various approximations are available for estimating a moisture amount (absolute humidity) per unit volume from relative humidity. In this example, the estimation is made using the relatively well-known Tetens formula.

Assuming the inflow moisture amount as $X_1$ [g/m$^3$], a temperature of the outside air OA as $t_1$[° C.], a relative humidity of the outside air OA as $RH_1$ [%], and a saturated vapor pressure of the outside air OA as $e_1$ [hPa], the control unit 70 obtains the inflow moisture amount $X_1$ by performing calculations using the following formulae (1) and (2).

In a case where the formula is applied by picking up a subscript 1 in any one of respective terms e, t, RH, X in the formulae (1) to (3), it is assumed that the subscript 1 is also picked up in other terms. In the same manner, in a case where the formula is applied by picking up a subscript 2 in any one of respective terms e, t, RH, X in the formulae (1) to (3), it is assumed that the subscript 2 is also picked up in other terms.

$$e_{1,2}(hPa) = 6.11 \times 10^{(7.5t1,2)/(t1,2+273.3)} \qquad (1)$$

-continued $$X_{1,2}(\text{g/m}^3) = (217 * e_{1,2}/(273.15 + t_{1,2})) \times (RH_{1,2}/100) \qquad (2)$$

In the same manner, the control unit 70 calculates a moisture amount per unit volume as an outflow moisture amount $X_2$ based on a temperature $t_2$ and a relative humidity $RH_2$ [%] of inside air IA received from the second thermo-hygro sensor 40. More specifically, assuming the outflow moisture amount as $X_2$ [g/m²], a temperature of the inside air IA as $t_2$ [° C.], a relative humidity of the inside air IA as $RH_2$ [%], and a saturated vapor pressure of the inside air IA as $e_2$ [hPa], the control unit 70 obtains the outflow moisture amount $X_2$ by performing calculations using the above-mentioned formulae (1) and (2).

The control unit 70 obtains the head perspiration amount Y (g/m³) by performing calculation by the following formula (3) based on the inflow moisture amount $X_1$ [g/m²] and the outflow moisture amount $X_2$ [g/m²] obtained by the above-mentioned calculation and a given (known) air volume F [m³/min] of the fan 30.

$$Y(\text{g/min}) = (X_2 - X_1) \times F(\text{m}^3/\text{min}) \qquad (3)$$

Further, the control unit 70 can also estimate the whole body perspiration amount based on the obtained head perspiration amount Y.

The control unit 70 includes "an inflow moisture amount calculation part" that calculates a moisture amount per unit volume as the above-mentioned inflow moisture amount $X_1$, "an outflow moisture amount calculation part" that calculates a moisture amount per unit volume as the outflow moisture amount $X_2$, and "a head perspiration calculation part" that calculates a head perspiration amount Y based on the inflow moisture amount $X_1$, the outflow moisture amount $X_2$, and the air volume F relating to discharging of the inside air IA by the fan 30. Further, the control unit may include "a whole body perspiration amount calculation part" that estimates a whole perspiration amount based on the calculated head perspiration amount Y.

The control unit 70 disposed in the perspiration amount measuring device may include all of the inflow moisture amount calculation part, the outflow moisture amount calculation part, the head perspiration amount calculation unit and the whole body perspiration amount calculation part. Alternatively, the management device disposed outside the perspiration amount measuring device may include some of or all of the inflow moisture amount calculation part, the outflow moisture amount calculation part, the head perspiration amount calculation part and the whole body perspiration amount calculation part.

Embodiment 3

Returning to FIG. 1, a perspiration amount measuring system 9 can be formed by combining the perspiration amount measuring device 1 and the helmet 100 according to the embodiment 1 (embodiment 3).

The perspiration amount measuring system 9 includes: the helmet 100; and the perspiration amount measuring device 1 according to the embodiment 1 mounted on an edge portion 102 of the helmet 100.

As the helmet 100, a commercially available general-use helmet can be adopted. For example, a work-use helmet used in general in construction work and the like can be named.

The helmet 100 includes an outer shell 101, an intermediate covering member 103, a brim 104 and the like. The outer shell 101 is a member that makes the external field E and the head H of the wearer WR spaced apart from each other, and protects the head H from the external field E. A helmet inside air flow path 110 is formed between the outer shell 101 and the head H of the wearer WR. The intermediate covering member 103 is, for example, an inner belt or the like, and supports the helmet 100 by bringing the helmet 100 into contact with the head. The intermediate covering member 103 has an opening, and vapor and hot air move back and forth between the head H and the helmet inside air flow path 110.

According to the perspiration amount measuring system 9 of the embodiment 3, as the perspiration amount measuring device, the perspiration amount measuring device 1 according to the embodiment 1 is used. Accordingly, the perspiration amount measuring system 9 acquires the advantageous effects substantially equal of the advantageous effects that the perspiration amount measuring device 1 according to the embodiment 1 possesses. With the use of such a perspiration amount measuring system 9, a head perspiration amount can be measured more accurately and hence, a measure against a heat stroke can be properly taken.

Heretofore, the description has been made with respect to the mode where the perspiration amount measuring system 9 is formed by using the perspiration amount measuring device 1 according to the embodiment 1. However, the embodiment 3 is not limited to such a mode, and the perspiration amount measuring system may be provided with the perspiration amount measuring device 2 according to the embodiment 2 (see FIG. 4), or the perspiration amount measuring devices 3, 4, 5 according to modifications described later.

The present invention has been described based on the above-mentioned embodiments heretofore. However, the present invention is not limited to the above-mentioned embodiments. The present invention can be carried out in various modes without departing from the gist of the present invention. For example, the following modifications are also conceivable.

Figure 8A:
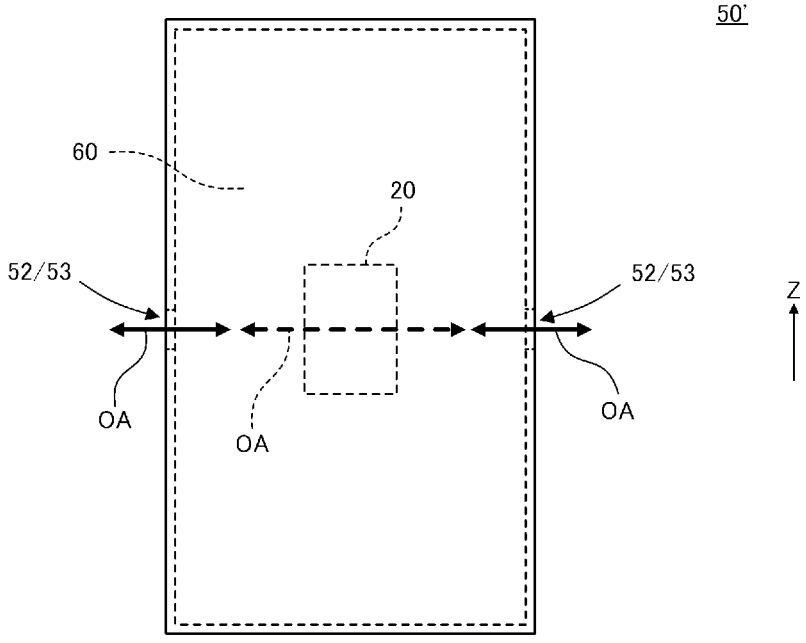
FIGS. 8A and 8B are formed of front views respectively illustrating sensor covers 50', 50'' of modifications 1,2.
Figure 8B:
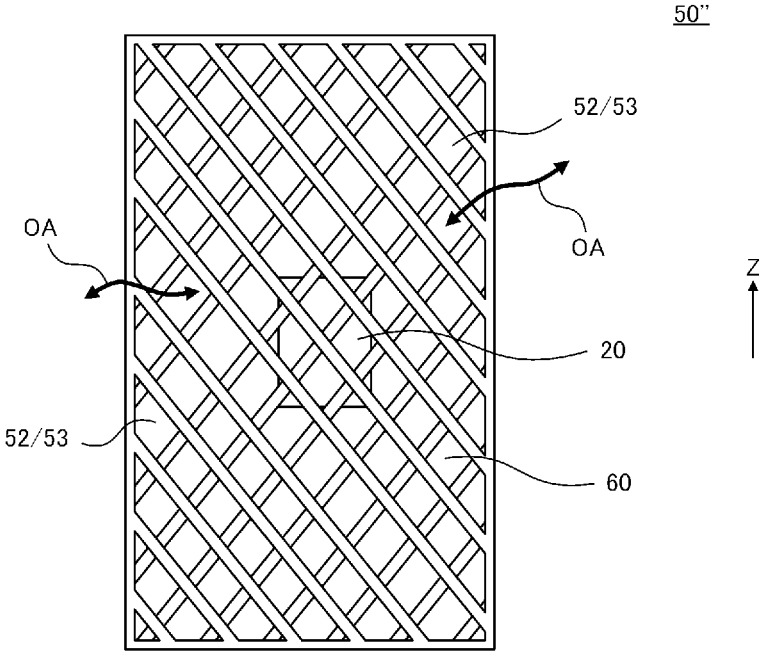
Figure 9:
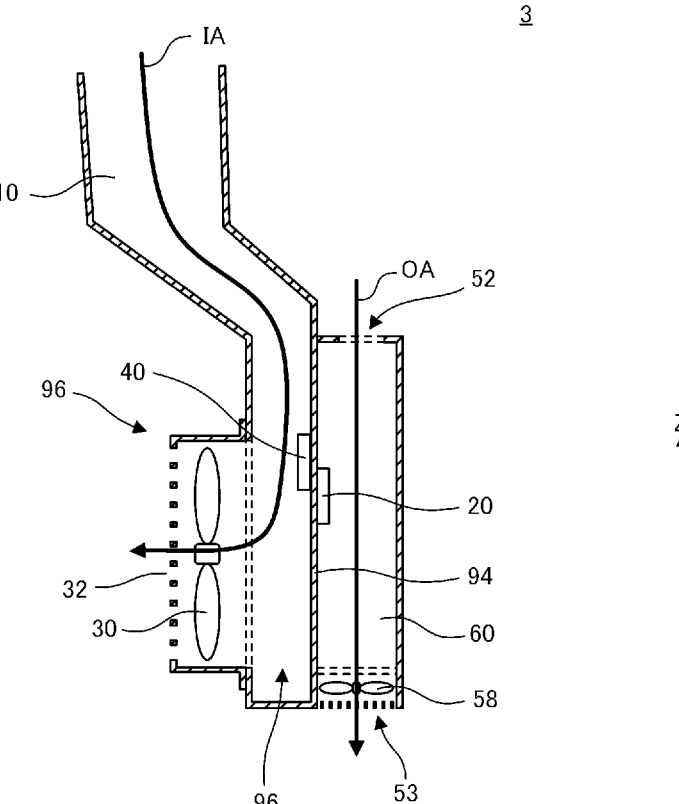
FIG. 9 is a schematic cross-sectional view illustrating a perspiration amount measuring device 3 according to a modification 3.
Figure 10:
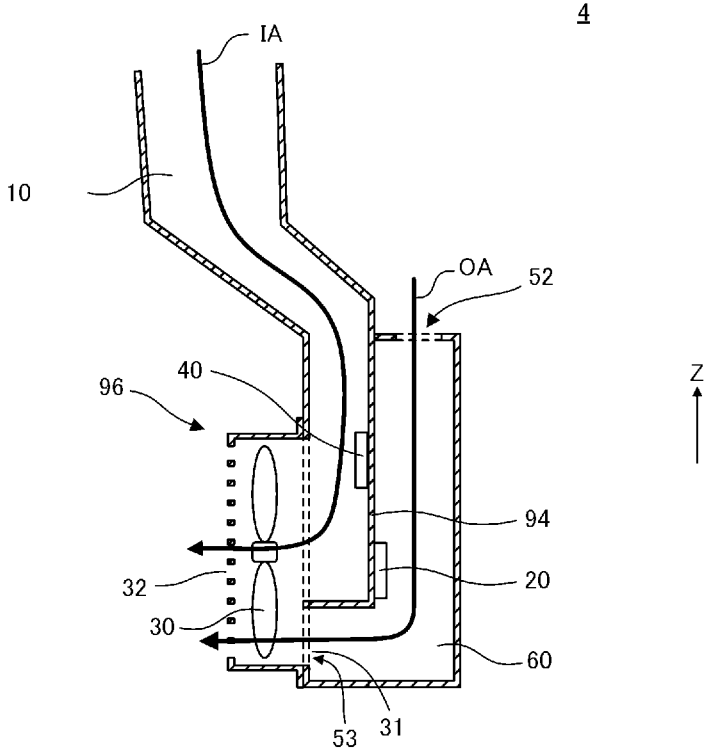
FIG. 10 is a schematic cross-sectional view illustrating a perspiration amount measuring device 4 according to a modification 4.
Figure 11:
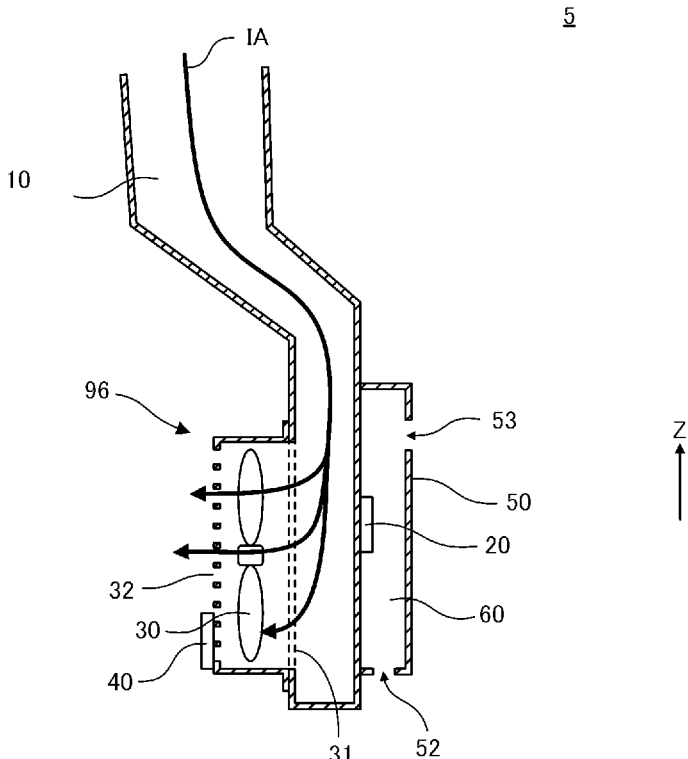
FIG. 11 is a schematic cross-sectional view illustrating a perspiration amount measuring device 5 according to a modification 5.

FIGS. 8A and 8B are front views illustrating sensor covers 50', 50" of the modifications 1, 2 respectively. FIG. 9 is a schematic cross-sectional view illustrating a perspiration amount measuring device 3 according to a modification 3. FIG. 10 is a schematic cross-sectional view illustrating a perspiration amount measuring device 4 according to a modification 4. FIG. 11 is a schematic cross-sectional view illustrating a perspiration amount measuring device 5 according to a modification 5.

(1) In the embodiment 1, the description has been made using the example where the outside air intake port 52 having a slit-like shape is formed on a front surface side of the sensor cover 50 (see FIG. 2). However, the present invention is not limited to such a configuration. For example, as illustrated in FIG. 8A, the configuration may also be adopted where a plurality of openings are formed in a side surface of the sensor cover 50', and these openings form the outside air intake port 52 (modification 1). Further, as illustrated in FIG. 8B, the configuration may be adopted where a front side of the sensor cover 50" is formed in a lattice shape (a reed screen shape, a meshed shape or the like) thus protecting the first thermo-hygro sensor 20 from the radiation of the external field E and the like while allowing the outside air OA to freely move back and forth (modification 2).

(2) In the embodiment 1, the configuration is adopted where only the outside air intake port 52 is formed in the sensor cover 50 so as to allow the outside air OA to flow in a natural manner. However, the present invention is not limited to such a configuration. For example, as illustrated in FIG. 9, the configuration may be adopted where a sensor-use fan 58 can be additionally mounted on a portion of the outside air intake port 52, and by operating the sensor-use fan 58, the flow of the outside air OA may be positively generated in a space 60 where the flow of the outside air OA is generated (modification 3).

Further, for example, as illustrated in FIG. 10, a configuration may be adopted where, on a fan suction port 31 side, a shield member 94 (a partition member 94) by which the air flow path 10 and the space 60 where the flow of the outside air OA is generated are separated from each other is disposed in an extending manner to an area where the shield member 94 is almost brought into contact with the fan 30, and the flow of the outside air OA may be positively generated by a suction force from a portion of the fan suction port 31 (modification 4).

(3) In the embodiment 1, the description has been made using the example where the second thermo-hygro sensor 40 is disposed in the closed portion 96 of the air flow path 10 (see FIG. 1). However, the present invention is not limited to such a configuration. For example, as illustrated in FIG. 11, the second thermo-hygro sensor 40 may be disposed outside of the air flow path 10 in a state where the second thermo-hygro sensor 40 is brought into contact with a fan discharge port 32 (modification 5). In the modification 5, the second thermo-hygro sensor 40 is disposed outside of the fan 30. Even in such a case, the second thermo-hygro sensor 40 is treated such that the second thermo-hygro sensor 40 is "disposed in the flow of the inside air".

(4) In the respective embodiments and the respective modifications, only the clip 92 is described as the helmet mounting means. However, the present invention is not limited to such a case.

For example, in addition to the fixing by the clip 92, the fixing may be reinforced by fastening the clip outer peripheral member 92b and an outer periphery of the edge portion of the helmet 100 together by a belt or the like not illustrated in the drawings. Further, the perspiration amount measuring device may be fixed using only a belt such that the perspiration amount measuring device is disposed between the belt and the outer shell 101 of the helmet 100, and the belt is wrapped around the helmet 100 together with the perspiration amount measuring device. Further, the perspiration amount measuring device may be mounted such that, for example, the outer shell 101 of the helmet 100 and the perspiration amount measuring device may be fixed to each other by adhesion using an adhesive agent.

(5) With respective to the perspiration amount measuring systems 9, 9' according to the respective embodiments and the respective modifications, the description has been made by treating the perspiration amount measuring system having the configuration where the helmet 100 and the perspiration amount measuring device 1, 2, 3, 4, 5 are formed as separate bodies from each other as the perspiration amount system 9, 9' in the narrow definition. However, the present invention is not limited to such a case. Also with respect to a dedicated helmet where the helmet 100 and the perspiration amount measuring device 1, 2, 3, 4, 5 are integrally formed with each other, the perspiration amount measuring system is treated equivalent to the perspiration amount measuring system 9, 9', and is included in the perspiration amount measuring systems 9, 9' of the present invention.

The invention claimed is:

1. A perspiration amount measuring system configured to measure a perspiration amount from a head of a wearer, the perspiration amount measuring system comprising:
an outer shell configured to cover the head to form an air flow path therebetween, inside air flowing through the air flow path and containing vapor generated from the head, the outer shell being configured to shield the inside air from outside air existing in an external field of the outer shell;
a first thermo-hygro sensor disposed at a place opened to the external field, the first thermo-hygro sensor being configured to measure a temperature and a relative humidity of the outside air;
a fan configured to suck the inside air in the air flow path and discharge the inside air to the external field; and
a second thermo-hygro sensor disposed at a position through which the inside air flows due to an operation of the fan, the second thermo-hygro sensor being configured to measure a temperature and a relative humidity of the inside air.

2. The perspiration amount measuring system according to claim 1, further comprising a sensor cover that covers the first thermo-hygro sensor.

3. The perspiration amount measuring system according claim 2,
wherein the sensor cover includes an outside air intake port and an outside air outlet port.

4. The perspiration amount measuring system according to claim 3,
wherein the first thermo-hygro sensor is disposed in a space where a flow of the outside air is generated.

5. The perspiration amount measuring system according to claim 4, further comprising a shield member having a communicating portion between the air flow path and the space.

6. The perspiration amount measuring system according to claim 5,
wherein the space is formed such that the outside air flows with a substantially constant flow amount adjacent to the first thermo-hygro sensor.

7. The perspiration amount measuring system according to claim 6,
wherein the first thermo-hygro sensor is disposed adjacent to the communicating portion and disposed at an upstream position of the communication portion with respect to the flow of the outside air.

8. The perspiration amount measuring system according to claim 6,
wherein the air flow path has a closed portion as a downstream end thereof, and the closed portion is located adjacent to the fan, and
the second thermo-hygro sensor is disposed adjacent to the fan.

9. The perspiration amount measuring system according to claim 2,
wherein the air flow path has a closed portion as a downstream end thereof, and the closed portion is located adjacent to the fan, and
the second thermo-hygro sensor is disposed adjacent to the fan.

10. The perspiration amount measuring system according to claim 2,
wherein the fan is disposed at a position where a discharge destination of air generated by the fan is in an area ranging from a back of the head to a back of a neck of the wearer while the outer shell covers the head.

11. The perspiration amount measuring system according to claim 2, further comprising:

a memory configured to store a program; and a processor configured to execute the program so as to:

calculate a first moisture amount per unit volume as an inflow moisture, amount based on the temperature and the relative humidity of the outside air measured by the first thermo-hygro sensor;

calculate a second moisture amount per unit volume as an outflow moisture amount, amount based on the temperature and the relative humidity of the inside air measured by the second thermo-hygro sensor;

calculate the perspiration amount from the head based on the inflow moisture amount, the outflow moisture amount, and an air volume relating to discharging of the inside air by the fan; and estimate a whole body perspiration amount of the wearer based on the perspiration amount from the head.

12. The perspiration amount measuring system according to claim 1, wherein the air flow path has a closed portion as a downstream end thereof, and the closed portion is located adjacent to the fan, and the second thermo-hygro sensor is disposed adjacent to the fan.

13. The perspiration amount measuring system according to claim 1, wherein the fan is disposed at a position where a discharge destination of air generated by the fan is in an area ranging from a back of the head to a back of a neck of the wearer while the outer shell covers the head.

14. The perspiration amount measuring system according to claim 1, further comprising:

a memory configured to store a program; and a processor configured to execute the program so as to:

calculate a first moisture amount per unit volume as an inflow moisture, amount based on the temperature and the relative humidity of the outside air measured by the first thermo-hygro sensor;

calculate a second moisture amount per unit volume as an outflow moisture amount based on the temperature and the relative humidity of the inside air measured by the second thermo-hygro sensor;

calculate the perspiration amount from the head based on the inflow moisture amount, the outflow moisture amount, and an air volume relating to discharging of the inside air by the fan; and estimate a whole body perspiration amount of the wearer based on the perspiration amount from the head.

15. A perspiration amount measuring device configured to measure a perspiration amount from a head of a wearer, the perspiration amount measuring device being attached at an edge of an outer shell, the outer shell configured to cover the head to form an air flow path therebetween, inside air flowing through the air flow path and containing vapor generated from the head, the outer shell being configured to shield the inside air from outside air existing in an external field of the outer shell, the perspiration amount measuring device comprising:

a first thermo-hygro sensor disposed at a place opened to the external field, the first thermo-hygro sensor being configured to measure a temperature and a relative humidity of the outside air;

a fan configured to suck the inside air in the air flow path and discharge the inside air to the external field; and a second thermo-hygro sensor disposed at a position through which the inside air flows due to an operation of the fan, the second thermo-hygro sensor being configured to measure a temperature and a relative humidity of the inside air.

16. The perspiration amount measuring device according to claim 15, further comprising:

a memory configured to store a program; and a processor configured to execute the program so as to:

calculate a first moisture amount per unit volume as an inflow moisture amount based on the temperature and the relative humidity of the outside air measured by the first thermo-hygro sensor;

calculate a second moisture amount per unit volume as an outflow moisture amount based on the temperature and the relative humidity of the inside air measured by the second thermo-hygro sensor;

calculate the perspiration amount from the head based on the inflow moisture amount, the outflow moisture amount, and an air volume relating to discharging of the inside air by the fan; and estimate a whole body perspiration amount of the wearer based on the perspiration amount from the head.

17. A perspiration amount measuring device configured to measure a perspiration amount from a head of a wearer, the perspiration amount measuring device comprising:

an air flow path through which inside air containing vapor generated from the head flows;

a first thermo-hygro sensor disposed at a place opened to an external field of the perspiration amount measuring device, the first thermo-hygro sensor being configured to measure a temperature and a relative humidity of outside air in the external field;

a shield member disposed between the air flow path and the external field, the shield member having a communicating portion through which the outside air flows;

a fan configured to:

suck the inside air in the air flow path and discharge the inside air to the external field; and suck the outside air through the communicating portion of the shield member to generate a flow of the outside air to the first thermo-hygro sensor; and a second thermo-hygro sensor disposed at a position through which the inside air flows due to an operation of the fan, the second thermo-hygro sensor being configured to measure a temperature and a relative humidity of the inside air.

18. The perspiration amount measuring device according to claim 17, further comprising:

a memory configured to store a program; and a processor configured to execute the program so as to:

calculate a first moisture amount per unit volume as an inflow moisture amount based on the temperature and the relative humidity of the outside air measured by the first thermo-hygro sensor;

calculate a second moisture amount per unit volume as an outflow moisture amount based on the temperature and the relative humidity of the inside air measured by the second thermo-hygro sensor;

calculate the perspiration amount from the head based on the inflow moisture amount, the outflow moisture amount, and an air volume relating to discharging of the inside air by the fan; and estimate a whole body perspiration amount of the wearer based on the perspiration amount from the head.

* * * * *